United States Patent [19]

Winkelmann et al.

[11] 4,031,232

[45] June 21, 1977

[54] 1-ALKYL-2-(PHENOXYMETHYL)-5-NITRO-IMIDAZOLES AND PROCESS FOR THEIR MANUFACTURE

[75] Inventors: Erhardt Winkelmann, Kelkheim, Taunus; Wolfgang Raether, Dreieichenhain, both of Germany

[73] Assignee: Hoechst Aktiengesellschaft, Frankfurt am Main, Germany

[22] Filed: Dec. 15, 1975

[21] Appl. No.: 641,091

[30] Foreign Application Priority Data

Dec. 16, 1974 Germany .......................... 2459395

[52] U.S. Cl. .............. 424/273; 260/309; 260/600 R; 260/612 D
[51] Int. Cl.$^2$ ............ A61K 31/415; C07D 233/94; C07D 233/95
[58] Field of Search ................. 260/309; 424/273

[56] References Cited

UNITED STATES PATENTS

| 3,682,951 | 8/1972 | Kreider | 260/309 |
|---|---|---|---|
| 3,761,491 | 9/1973 | Carlson et al. | 260/309 |
| 3,796,704 | 3/1974 | Metzger et al. | 260/309 |
| 3,828,065 | 8/1974 | Kreider | 260/309 |
| 3,910,925 | 10/1975 | Kreider | 260/309 |
| 3,922,277 | 11/1975 | Winkelmann et al. | 260/309 |

FOREIGN PATENTS OR APPLICATIONS

| 660,836 | 9/1965 | Belgium | 260/309 |
|---|---|---|---|
| 2,124,103 | 11/1971 | Germany | 260/309 |

OTHER PUBLICATIONS

Hoffer, Chem. Abst., 1968, vol. 68, No. 105198c.
Kreider, IV, Chem. Abst., 1975, vol. 82, No. 4254b.
Freiter et al., J. Heterocyclic Chem., 1973, vol. 10, pp. 391–394.
Swett et al., J. Med. Chem., 1970, vol. 13, pp. 968–970.

*Primary Examiner*—Natalie Trousof
*Attorney, Agent, or Firm*—Curtis, Morris & Safford

[57] ABSTRACT

1-Alkyl-2-(phenoxymethyl)-5-nitro-imidazoles are described as well as a process for their manufacture. The compounds are active against trichomonads and amoebae and are especially suitable for the treatment of *Fluor genitalis.*

12 Claims, No Drawings

1-ALKYL-2-(PHENOXYMETHYL)-5-NITRO-IMIDAZOLES AND PROCESS FOR THEIR MANUFACTURE

The present invention relates to 1-alkyl-2-(phenoxymethyl)-5-nitro-imidazoles and to a process for preparing them.

1-(2-Hydroxyethyl)-2-methyl-5-nitro-imidazole (Metronidazol) is used for the treatment of protozoal diseases, such as trichomoniasis and amoebiasis.

The present invention provides 1-alkyl-2-(phenoxymethyl)-5-nitro-imidazoles of the formula I

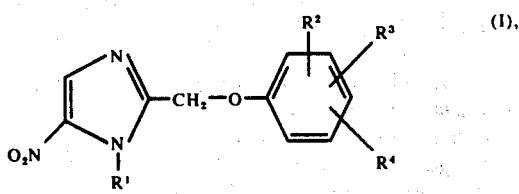

wherein
R$^1$ is methyl or ethyl,
R$^2$ is trifluoromethyl, trichloromethyl, nitro, cyano, methylsulfonyl or ethylsulfonyl, and
R$^3$ is hydrogen, fluorine, chlorine, bromine, iodine, trifluoromethyl, trichloromethyl, cyano or nitro, and
R$^4$ is hydrogen or methyl.

Preference is given to those compounds which carry — in the case of monosubstitution (R$^3$ and R$^4$ are hydrogen) — the substituent R$^2$ in the 2-, 3- or 4-position of the phenyl ring, or, in the case of disubstitution (R$^3$ is not hydrogen), carry 3,5-bis-trifluoromethyl or 3,5-bis-trichloromethyl, 2,4- or 2,6-dicyano and 2,4-, 2,6- or 3,5-dinitro, 2-halogeno-4-nitro, 2-halogeno-6-nitro, 4-halogeno-2-nitro, 2-trifluoromethyl-4-nitro, 4-trifluoromethyl-2-nitro, 2-halogeno-4-cyano, 2-halogeno-6-cyano, 4-halogeno-2-cyano as substituents in the phenyl ring.

The novel compounds are effective against various protozoa, especially against trichomonads, amoebae and trypanosoma. Moreover, they represent useful intermediate products for further syntheses.

The invention also provides a process for the preparation of 1-alkyl-2-(phenoxymethyl)-5-nitro-imidazoles of the formula I, which comprises A.
1a. Reacting 1-alkyl-2-subst.-methyl-5-nitro-imidazoles of the formula II

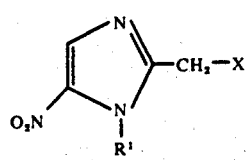

wherein R$^1$ has the above-mentioned meaning and X represents a halogen atom, such as fluorine, chlorine, bromine, or iodine, an acyloxy group, such as acetyloxy, propionyloxy, butyryloxy, benzoyloxy, nitrobenzoyloxy, or toloyloxy, or an arylsulfonyloxy group, such as benzene-sulfonyloxy, toluene-sulfonyloxy, or nitrobenzene-sulfonyloxy, with phenols of the formula III

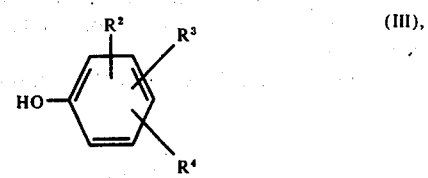

wherein R$^2$, R$^3$, R$^4$ have the meanings specified above, or 1b. reacting 1-alkyl-2-hydroxymethyl-5-nitro-imidazoles of the formula IV

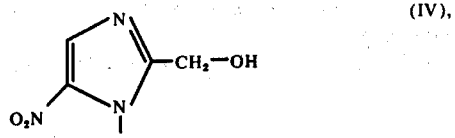

wherein R$^1$ has the above-specified meaning, with substituted benzenes of the formula V

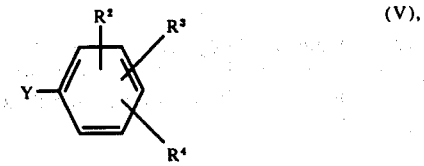

wherein Y represents preferably halogen, such as fluorine, chlorine, bromine, or iodine, or also acyloxy or arylsulfonyloxy, especially those groups mentioned above for X, and R$^2$, R$^3$, R$^4$ have the above-specified meanings, or B.
1a. reacting acetaldehyde-acetals of the formula VI

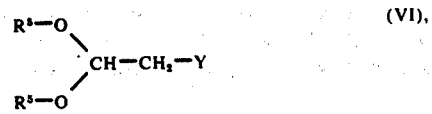

wherein R$^5$ represents a methyl or ethyl group and Y has the above-specified meaning, with phenols of the formula III, or 1b. reacting hydroxyacetaldehyde-acetals of the formula VII

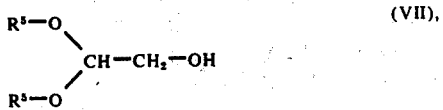

wherein R$^5$ has the above-mentioned meaning, with substituted benzenes of the formula V, in order to obtain 2. phenoxyacetaldehyde-acetals of the formula VIII

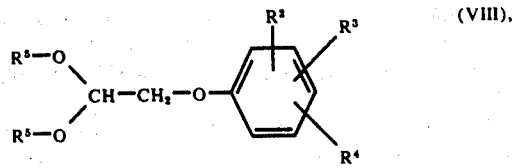

wherein $R^2$, $R^3$, $R^4$, $R^5$ have the above-specified meanings, treating the said compounds with aqueous formic acid to yield 3. phenoxyacetaldehydes of the formula IX

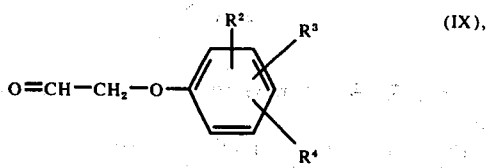

(optionally without isolation), reacting the same with aqueous ammonia and glyoxal or its functional derivatives to obtain 4. 2-phenoxymethylimidazoles of the formula X

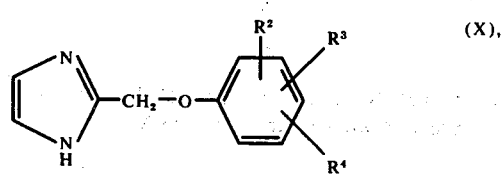

nitrating the product obtained with nitric acid, in the presence of water-binding agents, to form 5. 2-phenoxymethyl-4(5)-nitro-imidazoles of the formula XI

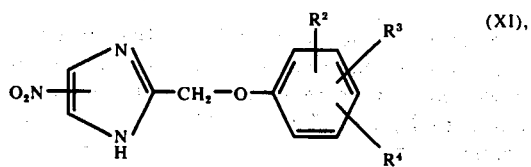

6. and alkylating the compound formed with alkylating agents, such as aryl-sulfonic acid-methyl-esters, for example, toluene-sulfonic acid-methyl-ester, with diazoalkanes, for example, diazo-methane, or preferably with dialkylsulfates of the formula XII $$(R^1-O)_2SO_2 \qquad (XII),$$

in order to obtain 1-alkyl-2-(phenoxymethyl)-5-nitro-imidazoles of the formula I.

As starting compounds of the formula II there may be mentioned, for example, 1-methyl-, 1-ethyl-2-chloro-, -2-bromo-, -2-iodo-methyl-5-nitro-imidazole, 1-methyl-, 1-ethyl-2-acetoxy, -2-benzoyloxy-, -2-(4-nitro-benzoyloxy)-methyl-5-nitro-imidazole, 1-methyl-, 1-ethyl-2-benzene-sulfonyloxy-, -2-(4-toluene-sulfonyloxy)-methyl-5-nitro-imidazole.

As starting compounds of the formula III there may be mentioned, for example, 2-, 3-, 4-trifluoromethyl-, -trichloromethyl-phenol, 3,5-bis-trifluoromethyl-, -trichloromethyl-phenol, 2-, 3-, 4-nitro-, -cyano-, -methylsulfonyl-, -ethyl-sulfonyl-phenol, 2,4-, 2,6-dinitro-, -dicyano-phenol, 2-fluoro-, -chloro-, -bromo-, -iodo-4-nitro-, -4-cyano-phenol, 2-fluoro-, -chloro-, -bromo-, -iodo-6-nitro-, -6-cyano-phenol, 4-fluoro-, -chloro-, -bromo-, -iodo-2-nitro-, -2-cyano-phenol, 2-trifluoromethyl-4-nitro-phenol, 4-trifluoromethyl-2-nitro-phenol.

As starting compounds of the formula IV there may be mentioned, for example, 1-methyl-, 1-ethyl-2-hydroxymethyl-5-nitro-imidazole.

As starting compounds of the formula V there may be mentioned, for example, 1-fluoro-, -chloro-, -bromo-, -iodo-, 1-acetoxy-, -benzoyloxy-, -(4-nitrobenzoyloxy)-, 1-benzene-sulfonyloxy-, -(4-toluene-sulfonyloxy)-, 2-, 3-, 4-nitro-, -cyano-, methylsulfonyl-, ethylsulfonyl-benzene, 2,4-, 2,6-dinitro-, -dicyano-benzene, 2-fluoro-, -chloro-, -bromo-, -iodo-4-nitro-, -4-cyano-benzene, 2-fluoro-, -chloro-, -bromo-, -iodo-4-nitro-, -4-cyano-benzene, 2-fluoro-, -chloro-, -bromo-, -iodo-6-nitro-, -6-cyano-benzene, 4-fluoro-, -chloro-, -bromo-, -iodo-2-nitro-, -2-cyano-benzene, 2-trifluoromethyl-4-nitro-phenol, 4-trifluoromethyl-2-nitro-benzene, 1-acetoxy-, -benzoyloxy-, -(4-nitro-benzoyloxy)-, 1-benzene-sulfonyloxy-, -(4-toluene-sulfonyloxy)-, 2-, 3-, 4-trifluoromethyl-, -trichloromethyl-benzene, 3,5-bis-trifluoromethyl-, -trichloromethyl-benzene.

As starting compounds of the formula VI there may be mentioned, for example, chloro-, bromo-, iodo-acetaldehyde-dimethyl-, -diethyl-acetal.

As starting compounds of the formula VII there may be mentioned, for example, hydroxy-acetaldehyde-dimethyl-, -diethyl-acetal.

As starting compounds of the formula VIII there may be mentioned, for example, 2-, 3-, 4-trifluoromethyl-, -trichloromethyl-phenoxy-, 3,5-bis-trifluoromethyl-, -trichloromethyl-phenoxy-, 2-, 3-, 4-nitro-, cyano-, -methylsulfonyl-, -ethylsulfonyl-phenoxy-, 2,4-, 2,6-dinitro-, -dicyano-phenoxy-, 2-fluoro-, -chloro-, -bromo-, -iodo-4-nitro-, -4-cyano-phenoxy-, 2-fluoro-, -chloro-, -bromo-, -iodo-6-nitro-, -6-cyano-phenoxy-, 4-fluoro-, -chloro-, -bromo-, -iodo-2-nitro-, -2-cyano-phenoxy-, 2-trifluoromethyl-4-nitro-phenol, 4-trifluoromethyl-2-nitro-phenoxy-acetaldehyde-dimethyl-, -diethyl-acetal.

As starting compounds of the formula IX there may be mentioned, for example, 2-, 3-, 4-trifluoromethyl-, -trichloromethyl-phenoxy-, 3,5-bis-trifluoromethyl-, -trichloromethyl-phenoxy-, 2-, 3-, 4-nitro-, cyano-, -methylsulfonyl-, -ethylsulfonyl-phenoxy-, 2,4-, 2,6-dinitro-, -dicyano-phenoxy-, 2-fluoro-, -chloro-, -bromo-, -iodo-4-nitro-, -4-cyano-phenoxy-, 2-fluoro-, -chloro-, -bromo-, -iodo-6-nitro-, -6-cyano-phenoxy-, 4-fluoro-, -chloro-, -bromo-, -iodo-2-nitro-, -2-cyano-phenoxy-, 2-trifluoromethyl-4-nitro-phenol, 4-trifluoromethyl-2-nitro-phenoxy-acetaldehyde.

As functional glyoxal derivatives there may be mentioned, for example, glyoxal sulfate and glyoxal disodium bisulfite.

As starting compounds of the formula X there may be mentioned, for example, 2-(2-, 3-, 4-trifluoromethyl-, -trichloromethyl-phenoxymethyl-, 2-(3,5-bis-trifluoromethyl-, -trichloromethyl-phenoxymethyl-, 2-(2-, 3-, 4-nitro-, -cyano-, -methylsulfonyl-, -ethylsulfonyl-phenoxymethyl-, 2-(2,4-, 2,6-dinitro-, -dicyano-phenoxymethyl-, 2-(2-fluoro-, -chloro-, -bromo-, -iodo-4-nitro-, -4-cyano-phenoxy-methyl-, 2-(2-fluoro-, -chloro-, -bromo-, -iodo-6-nitro-, -6-cyano-phenoxy-methyl-, 2-(4-fluoro-, -chloro-, -bromo-, -ioco-2-nitro-, -2-cyano-phenoxy-methyl-, 2-(2-trifluoromethyl-4-nitro-phenol, 4-trifluoromethyl-2-nitro-phenoxymethyl-imidazole.

As starting compounds of the formula XI there may be mentioned, for example, 2-(2-, 3-, 4-trifluoromethyl-, -trichloromethyl-phenoxymethyl-, 2-(3,5-bis-trifluoromethyl-, -trichloromethyl-phenoxymethyl-, 2-(2-, 3-, 4-nitro-, -cyano-, -methylsulfonyl-, -ethylsulfonyl-phenoxymethyl-, 2-(2,4-, 2,6-dinitro-, -dicyanophenoxymethyl-, 2-(2-fluoro-, -chloro-, -bromo-, -iodo-4-nitro-, -4-cyano-phenoxymethyl-, 2-(2-fluoro-, -chloro-, -bromo-, -iodo-6-nitro-, -6-cyano-, phenoxymethyl-, 2-(4-fluoro-, -chloro-, -bromo-, -iodo-2-nitro-, -2-cyano-phenoxymethyl-, 2-(2-trifluoromethyl-4-nitro-phenol, 4-trifluoromethyl-2-nitro-phenoxymethyl-4(5)-nitro-imidazole.

As starting compounds of the formula XII there may be mentioned, for example, dimethyl- or diethyl-sulfate.

The reactions are suitably carried out in equimolar amounts. In the case of volatile reactants, however, excess amounts should be used.

The reactions are advantageously carried out in a solvent or distributing agent.

For the reaction of the step A. (1a/b) there may be mentioned preferably polar solvents, for example, alcohols, such as methanol, ethanol, propanol, isopropanol, 2-methoxy-, or 2-ethoxy-ethanol, ethers, such as tetrahydrofuran, dioxan, ethylene-glycol-dimethylether, or -diethylether, ketones, such as acetone, diethylketone, methylethylketone, or methyl-isobutylketone, amides, such as dimethylformamide, or dimethylacetamide, N-methylpyrrolidone, tetramethylurea, hexamethylphosphoric acid-triamide, dimethylsulfoxide, heterocyclic bases, such as pyridine, picoline, or quinoline.

The phenols of the formula III used for the reaction can be used in their free form or as alkali metal salts. In the reaction of phenols, the use of acid-binding agents is recommended.

As acid-binding agents there may be mentioned bases, such as triethylamine or pyridine, as well as alkali metal and alkaline earth metal carbonates and -bicarbonates, -hydroxides and -alkoxides, such as -methoxides, -ethoxides or -butoxides.

The reaction temperatures may generally be in the range of from 0° to 150° C, preferably from 20° to 80° C. The reaction times are from a few minutes to several hours, depending on the temperature range.

In the reaction of step B (2) there may be mentioned as solvents, for example, ethers, such as tetrahydrofuran, dioxan, ethylene-glycol-dimethylether, -diethylether, di-isopropylether, or di-isobutylether, amides, such as dimethylformamide, dimethylacetamide, N-methylpyrrolidone, tetramethylurea, hexamethylphosphoric acid-triamide, dimethylsulfoxide.

The phenols of the formula III used for the reaction may be used in their free form or as alkali metal salts. In the reaction of phenols, the use of acid-binding agents is recommended.

As acid-binding agents there may be mentioned bases, such as triethylamine or pyridine, as well as alkali metal and alkaline earth metal carbonates and -bicarbonates, -hydroxides and -alkoxides, such as -methoxides, -ethoxides, -butoxides.

The reaction temperatures may generally be in the range of from 20° to 150° C, preferably from 60° to 100° C.

The reaction times are from a few minutes to several hours, depending on the temperature range.

In the reaction of step B (3), excess aqueous formic acid is used as solvent and diluent.

The reaction temperatures may generally be in the range of from 20° to 150° C, preferably from 60° to 100° C.

The reaction times are from 1 to several hours, depending on the temperature range.

In the reaction of step B (4) there may be mentioned mixtures of water and alcohols, for example, methanol, ethanol, propanol, or isopropanol as solvents in order to ensure a homogeneous solution of the reactant phenoxyacetaldehydes of the formula IX, glyoxal and ammonia.

The reaction temperatures are in the range of from 0° to 50° C; the reaction is advantageously carried out at room temperature.

The reaction times are from a few minutes to several hours.

For the reaction of step B (5) the reactants nitric acid/sulfuric acid serve as solvents and distributing agents. As water-binding agent there may be used acetic acid anhydride, phosphorus pentoxide or sulfur trioxide (oleum).

The nitration is carried out at a temperature in the range of from −10° to 50° C, preferably from −10° to 0° C. In this reaction a large excess of nitric acid is advantageously avoided, or use is made of alkali metal salts of nitric acid, instead of using concentrated nitric acid. The nitration time is from a few minutes to several hours, depending on the reaction temperature.

For the reaction of step B (6) there may be mentioned preferably aprotic solvents, for example, ethers, such as tetrahydrofuran, dioxan, ethylene-glycol-dimethylether, or -diethylether, aromatic hydrocarbons, such as benzene, toluene, or xylene. However, the alkylation reaction can also be carried out without a solvent. In this case, excess dialkylsulfate is used as diluent.

The alkylation temperatures are in the range of from 50° to 150° C, preferably from 80° to 110° C. The reaction times are from a few minutes to several hours.

The products of the invention are isolated according to the usual methods, by distilling off the solvents used or by diluting the reaction solution with water. Optionally, the products may be purified by a recrystallization from an appropriate solvent or solvent mixture.

1-Alkyl-2-(phenoxymethyl)-5-nitro-imidazoles of the formula I are suitable for the treatment of protozoal diseases in mammals, as they are caused, for example, by infections with *Trichomonas vaginalis*, *Entamoeba histolytica* and *Trypanosoma cruci*, *T. brucei*, *T. congolense*. The novel compounds of the invention can be administered orally or locally. The dosage unit for oral administration is given in the usual forms for pharmaceutical preparations, for example, tablets or capsules containing, per daily dosage unit, about 10 to 750 mg, preferably from 30 to 300 mg, of the active substance in combination with usual carrier substances, diluents and/or constituents. For local application, jellies, creams, ointments or suppositories are useful.

The novel products of the invention are well compatible and are marked by a reliable activity against trichomonads and amoebae in vivo which is clearly superior to that of the known comparative preparation of Metronidazol.

The products of the invention are especially suitable for treatment of *Fluor genitalis*. For the local treatment, they are preferably processed into vaginal suppositories (ovula) or vaginal tablets, which contain the active substance in an amount of from 150 to 500 mg per dosage unit.

The following Examples serve to illustrate the invention.

EXAMPLES OF PREPARATION
PROCESS A 1a)
EXAMPLE 1

1-Methyl-2(4-nitrophenoxymethyl)-5-nitro-imidazole 10.6 Grams (0.06 mole) of 1-methyl-2-chloromethyl-5-nitro-imidazole were dissolved in 30 ml of dimethylacetamide and were introduced at the same time, while stirring, to a suspension of 9.6 g (0.06 mole) of 4-nitrophenol-sodium salt in 20 ml of dimethylacetamide. Subsequently the reaction mixture was heated for 30 minutes on a steam bath at a temperature of from 70° to 80° C, while stirring, in which process all of the constituents were dissolved and sodium chloride started to separate. After having been cooled to room temperature, the reaction solution was poured into ice water, the precipitate that had separated was suction-filtered, was washed with water and was recrystallized from ethanol while adding charcoal.

Thus, 14 g (=84% of the theory) of 1-methyl-2-(4-nitro-phenoxymethyl)-5-nitro-imidazole were obtained in the form of cream-colored crystals which had a melting point of 150° C.

EXAMPLE 2

1-Methyl-2-(4-cyanophenoxymethyl)-5-nitro-imidazole 10.6 Grams (0.06 mole) of 1-methyl-2-chloromethyl-5-nitro-imidazole were suspended, together with 7.1 g (0.06 mole) of 4-cyanophenol, in the presence of 5.6 g (0.04 mole) of potassium carbonate, in 50 ml of dimethylacetamide. The suspension was heated for 2 hours, while stirring, at a temperature of from 50° to 60° C and was worked up as has been described in Example 1.

Thus, 12.5 g (=81% of the theory) of 1-methyl-2-(4-cyano-phenoxymethyl)-5-nitro-imidazole were obtained in the form of cream-colored crystals which had a melting point of 130° C.

EXAMPLE 3

1-Methyl-2-(4-methylsulfonyl-phenoxymethyl)-5-nitro-imidazole 17.6 Grams (0.1 mole) of 1-methyl-2-chloromethyl-5-nitro-imidazole were heated for 2 hours at a temperature of from 50° to 60° C, while stirring thoroughly, as has been described in detail in Example 2 above, together with 17.2 g (0.1 mole) of 4-methylsulfonyl-phenol in 50 ml of dimethylacetamide, in the presence of 13.8 g (0.1 mole) of potassium carbonate. According to the processing method described in Example 1 above, 22.5 g (=73% of the theory) of 1-methyl-2-(4-methylsulfonyl-phenoxymethyl)-5-nitro-imidazole were obtained in the form of white crystals having a melting point of 157° C.

The 1-methyl-2-chloromethyl-5-nitro-imidazole used as starting compound was prepared according to German Offenlegungsschrift No. 1,595,929 by reacting 1-methyl-2-hydroxymethyl-5-nitro-imidazole (cf. German Offenlengungsschrift No. 1,470,102) with thionylchloride.

The 4-methylsulfonylphenol used as starting compound was prepared from 4-methylthiophenol by way of oxidation using hydrogen superoxide in glacial acetic acid.

The following compounds were obtained in a good yield according to the same method:

EXAMPLE 4

1-Methyl-2-(2-nitrophenoxymethyl)-5-nitro-imidazole having a melting point of 149° C, from 1-methyl-2-chloromethyl-5-nitro-imidazole and 2-nitrophenol;

EXAMPLE 5

1-methyl-2-(3-nitrophenoxymethyl)-5-nitro-imidazole having a melting point of 153° C. from 1-methyl-2-chloromethyl-5-nitro-imidazole and 3-nitrophenol;

EXAMPLE 6

1-methyl-2-(2-chloro-4-nitrophenoxymethyl)-5-nitro-imidazole having a melting point of 138° C, from 1-methyl-2-chloromethyl-5-nitro-imidazole and 2-chloro-4-nitrophenol;

EXAMPLE 7

1-methyl-2-(4-chloro-2-nitrophenoxymethyl)-5-nitro-imidazole having a melting point of 179° C, from 1-methyl-2-chloromethyl-5-nitro-imidazole and 4-chloro-2-nitrophenol.

According to the same method, the following compounds were obtained in a good yield:
8. 1-Methyl-2-(2-trifluoromethylphenoxymethyl)-5-nitro-imidazole;
9. 1-methyl-2-(2-trichloromethylphenoxymethyl)-5-nitro-imidazole;
10. 1-methyl-2-(3-trifluoromethylphenoxymethyl)-5-nitro-imidazole, m.p. 80° C;
11. 1-methyl-2-(3-trichloromethylphenoxymethyl)-5-nitro-imidazole;
12. 1-methyl-2-(4-trifluoromethylphenoxymethyl)-5-nitro-imidazole, m.p. 95° C;
13. 1-methyl-2-(4-trichloromethylphenoxymethyl)-5-nitro-imidazole;
14. 1-methyl-2-(3,5-bis-trifluoromethylphenoxymethyl)-5-nitro-imidazole, m.p. 102° C;
15. 1-methyl-2-(3,5-bis-trichloromethylphenoxymethyl)-5-nitro-imidazole;
16. 1-methyl-2-(2,4-dinitrophenoxymethyl)-5-nitro-imidazole, m.p. 196° C, from 1-methyl-2-chloromethyl-5-nitro-imidazole and 2,4-dinitrophenol;
17. 1-methyl-2-(2,6-dinitrophenoxymethyl)-5-nitro-imidazole;
18. 1-methyl-2-(3,5-dinitrophenoxymethyl)-5-nitro-imidazole;
19. 1-methyl-2-(2-cyanophenoxymethyl)-5-nitro-imidazole, m.p. 192° C, from 1-methyl-2-chloromethyl-5-nitro-imidazole and 2-cyano-phenol;
20. 1-methyl-2-(3-cyanophenoxymethyl)-5-nitro-imidazole, m.p. 155° C, from 1-methyl-2-chloromethyl-5-nitro-imidazole and 3-cyano-phenol;
21. 1-methyl-2-(2,4-dicyanophenoxymethyl)-5-nitro-imidazole;
22. 1-methyl-2-(2,6-dicyanophenoxymethyl)-5-nitro-imidazole;
23. 1-methyl-2-(2-methylsulfonylphenoxymethyl)-5-nitro-imidazole;
24. 1-methyl-2-(3-methylsulfonylphenoxymethyl)-5-nitro-imidazole;
25. 1-methyl-2-(2-ethylsulfonylphenoxymethyl)-5-nitro-imidazole;

26. 1-methyl-2-(3-ethylsulfonylphenoxymethyl)-5-nitro-imidazole;
27. 1-methyl-2-(4-ethylsulfonylphenoxymethyl)-5-nitro-imidazole;
28. 1-methyl-2-(2-fluoro-4-nitrophenoxymethyl)-5-nitro-imidazole;
29. 1-methyl-2-(2-bromo-4-nitrophenoxymethyl)-5-nitro-imidazole;
30. 1-methyl-2-(2-iodo-4-nitrophenoxymethyl)-5-nitro-imidazole;
31. 1-methyl-2-(2-fluoro-4-cyanophenoxymethyl)-5-nitro-imidazole;
32. 1-methyl-2-(2-chloro-4-cyanophenoxymethyl)-5-nitro-imidazole;
33. 1-methyl-2-(2-bromo-4-cyanophenoxymethyl)-5-nitro-imidazole;
34. 1-methyl-2-(2-fluoro-6-nitrophenoxymethyl)-5-nitro-imidazole;
35. 1-methyl-2-(2-chloro-6-nitrophenoxymethyl)-5-nitro-imidazole;
36. 1-methyl-2-(2-bromo-6-nitrophenoxymethyl)-5-nitro-imidazole;
37. 1-methyl-2-(2-iodo-6-nitrophenoxymethyl)-5-nitro-imidazole;
38. 1-methyl-2-(2-fluoro-6-cyanophenoxymethyl)-5-nitro-imidazole;
39. 1-methyl-2-(2-chloro-6-cyanophenoxymethyl)-5-nitro-imidazole;
40. 1-methyl-2-(2-bromo-6-cyanophenoxymethyl)-5-nitro-imidazole;
41. 1-methyl-2-(4-fluoro-2-nitrophenoxymethyl)-5-nitro-imidazole;
42. 1-methyl-2-(4-bromo-2-nitrophenoxymethyl)-5-nitro-imidazole;
43. 1-methyl-2-(4-iodo-2-nitrophenoxymethyl)-5-nitro-imidazole;
44. 1-methyl-2-(4-fluoro-2-cyanophenoxymethyl)-5-nitro-imidazole;
45. 1-methyl-2-(4-chloro-2-cyanophenoxymethyl)-5-nitro-imidazole;
46. 1-methyl-2-(4-bromo-2-cyanophenoxymethyl)-5-nitro-imidazole;
47. 1-methyl-2-(2-trifluoromethyl-4-nitrophenoxymethyl)-5-nitro-imidazole, m.p. 153° C, from 1-methyl-2-hydroxymethyl-5-nitro-imidazole and 2-trifluoromethyl-4-nitro-fluorobenzene;
48. 1-ethyl-2-(4-cyanophenoxymethyl)-5-nitro-imidazole, m.p. 143° C, from 1-ethyl-2-chloromethyl-5-nitro-imidazole and 4-cyanophenol.

According to the same method, the following compounds were obtained in a good yield:
49. 1-ethyl-2-(2-cyanophenoxymethyl)-5-nitro-imidazole;
50. 1-ethyl-2-(3-cyanophenoxymethyl)-5-nitro-imidazole;
51. 1-ethyl-2-(2-nitrophenoxymethyl)-5-nitro-imidazole;
52. 1-ethyl-2-(3-nitrophenoxymethyl)-5-nitro-imidazole;
53. 1-ethyl-2-(4-nitrophenoxymethyl)-5-nitro-imidazole;
54. 1-ethyl-2-(2-trifluoromethylphenoxymethyl)-5-nitro-imidazole;
55. 1-ethyl-2-(2-trichloromethylphenoxymethyl)-5-nitro-imidazole;
56. 1-ethyl-2-(3-trifluoromethylphenoxymethyl)-5-nitro-imidazole;
57. 1-ethyl-2-(3-trichloromethylphenoxymethyl)-5-nitro-imidazole;
58. 1-ethyl-2-(4-trifluoromethylphenoxymethyl)-5-nitro-imidazole;
59. 1-ethyl-2-(4-trichloromethylphenoxymethyl)-5-nitro-imidazole;
60. 1-ethyl-2-(3,5-bis-trifluoromethylphenoxymethyl)-5-nitro-imidazole;
61. 1-ethyl-2-(3,5-bis-trichloromethylphenoxymethyl)-5-nitro-imidazole;
62. 1-ethyl-2-(2,4-dinitrophenoxymethyl)-5-nitro-imidazole;
63. 1-ethyl-2-(2,6-dinitrophenoxymethyl)-5-nitro-imidazole;
64. 1-ethyl-2-(3,5-dinitrophenoxymethyl)-5-nitro-imidazole;
65. 1-ethyl-2-(2,4-dicyanophenoxymethyl)-5-nitro-imidazole;
66. 1-ethyl-2-(2,6-dicyanophenoxymethyl)-5-nitro-imidazole;
67. 1-ethyl-2-(2-methylsulfonylphenoxymethyl)-5-nitro-imidazole;
68. 1-ethyl-2-(3-methylsulfonylphenoxymethyl)-5-nitro-imidazole;
69. 1-ethyl-2-(4-methylsulfonylphenoxymethyl)-5-nitro-imidazole;
70. 1-ethyl-2-(2-ethylsulfonylphenoxymethyl)-5-nitro-imidazole;
71. 1-ethyl-2-(3-ethylsulfonylphenoxymethyl)-5-nitro-imidazole;
72. 1-ethyl-2-(4-ethylsulfonylphenoxymethyl)-5-nitro-imidazole;
73. 1-ethyl-2-(2-fluoro-4-nitrophenoxymethyl)-5-nitro-imidazole;
74. 1-ethyl-2-(2-chloro-4-nitrophenoxymethyl)-5-nitro-imidazole;
75. 1-ethyl-2-(2-bromo-4-nitrophenoxymethyl)-5-nitro-imidazole;
76. 1-ethyl-2-(2-iodo-4-nitrophenoxymethyl)-5-nitro-imidazole;
77. 1-ethyl-2-(2-fluoro-4-cyanophenoxymethyl)-5-nitro-imidazole;
78. 1-ethyl-2-(2-chloro-4-cyanophenoxymethyl)-5-nitro-imidazole;
79. 1-ethyl-2-(2-bromo-4-cyanophenoxymethyl)-5-nitro-imidazole;
80. 1-ethyl-2-(2-fluoro-6-nitrophenoxymethyl)-5-nitro-imidazole;
81. 1-ethyl-2-(2-chloro-6-nitrophenoxymethyl)-5-nitro-imidazole;
82. 1-ethyl-2-(2-bromo-6-nitrophenoxymethyl)-5-nitro-imidazole;
83. 1-ethyl-2-(2-iodo-6-nitrophenoxymethyl)-5-nitro-imidazole;
84. 1-ethyl-2-(2-fluoro-6-cyanophenoxymethyl)-5-nitro-imidazole;
85. 1-ethyl-2-(2-chloro-6-cyanophenoxymethyl)-5-nitro-imidazole;
86. 1-ethyl-2-(2-bromo-6-cyanophenoxymethyl)-5-nitro-imidazole;
87. 1-ethyl-2-(4-fluoro-2-nitrophenoxymethyl)-5-nitro-imidazole;
88. 1-ethyl-2-(4-chloro-2-nitrophenoxymethyl)-5-nitro-imidazole;
89. 1-ethyl-2-(4-bromo-2-nitrophenoxymethyl)-5-nitro-imidazole;
90. 1-ethyl-2-(4-iodo-2-nitrophenoxymethyl)-5-nitro-imidazole;

91. 1-ethyl-2-(4-fluoro-2-cyanophenoxymethyl)-5-nitro-imidazole;
92. 1-ethyl-2-(4-chloro-2-cyanophenoxymethyl)-5-nitro-imidazole;
93. 1-ethyl-2-(4-bromo-2-cyanophenoxymethyl)-5-nitro-imidazole;
94. 1-ethyl-2-(2-trifluoromethyl-4-nitrophenoxymethyl)-5-nitro-imidazole;
95. 1-ethyl-2-(3-trifluoromethyl-4-nitrophenoxymethyl)-5-nitro-imidazole;
96. 1-ethyl-2-(4-trifluoromethyl-2-nitrophenoxymethyl)-5-nitro-imidazole;
97. 1-methyl-2-(3-methyl-4-nitrophenoxymethyl)-5-nitro-imidazole, m.p. 130° C, from 17.6 g (0.1 mole) of 1-methyl-2-chloromethyl-5-nitro-imidazole (MCNI) and 15.3 g (0.1 mole) of 3-methyl-4-nitrophenol;
98. 1-methyl-2-(3-methyl-4-cyanophenoxymethyl)-5-nitro-imidazole, m.p. 124° C, from 17.6 g (0.1 mole) of MCNI and 13.3 g (0.1 mole) of 3-methyl-4-cyanophenol;
99. 1-methyl-2-(3-methyl-4-methylsulfonyl-phenoxymethyl)-5-nitro-imidazole, m.p. 141° C, from 17.6 g (0.1 mole) of MCNI and 18.6 g (0.1 mole) of 3-methyl-4-methylsulfonylphenol.

The preparation is effected in a manner analogous to Example 2 in 50 ml of dimethylacetamide, by heating at a temperature of from 50° to 60° C for 2 hours, in the presence of 13.8 g (0.1 mole) of potassium carbonate.

(Process A 1b)

EXAMPLE 100

1-Methyl-2-(4-trifluoromethyl-2-nitrophenoxymethyl)-5-nitro-imidazole 15.7 Grams (0.1 mole) of 1-methyl-2-hydroxymethyl-5-nitro-imidazole and 21.0 g (0.1 mole) of 2-nitro-4-trifluoromethylfluoro-benzene dissolved in 100 ml of butanone-2 were mixed with 15 g of triethylamine and were heated for 2 hours on a steam bath. The crystals obtained when the solution had been cooled were suction-filtered, were washed with water and were recrystallized from a little isopropanol, while adding charcoal. As a result, 25 g (=72% of the theory) of 1-methyl-2-(4-trifluoromethyl-2-nitrophenoxymethyl)-5-nitro-imidazole were obtained in the form of yellowish crystals having a melting point of 126° C.

Instead of butanone-2 as the reaction medium, dimethylformamide could also be used, and instead of the auxiliary base of triethylamine, potassium carbonate could be used with the same yield of the final product. In this case, the reaction time was only 5 minutes at a temperature of 120° C.

In an analogous manner, all the compounds specified according to the process A (1a) could be prepared in accordance with the process A (1b) described, preferably with Y = fluorine in the formula V:

EXAMPLE 101

1-Methyl-2-(2-trifluoromethyl-4-nitrophenoxymethyl)-5-nitro-imidazole m.p. 153° C, from 1-methyl-2-hydroxymethyl-5-nitro-imidazole and 2-trifluoromethyl-4-nitro-fluorobenzene.

EXAMPLE 102

1-Methyl-2-(4-nitrophenoxymethyl)-5-nitro-imidazole m.p. 150° C, from 15.7 g (0.1 mole) of 1-methyl-2-hydroxymethyl-5-nitro-imidazole (MHNI) and 14.1 g (0.1 mole) of 4-nitrofluorobenzene.

EXAMPLE 103

1-Methyl-2-(4-cyanophenoxymethyl)-5-nitro-imidazole m.p. 130° C, from 15.7 g (0.1 mole) of MHNI and 12.1 g (0.1 mole) of 4-cyanofluorobenzene.

EXAMPLE 104

1-Methyl-2-(2-chloro-4-nitrophenoxymethyl)-5-nitro-imidazole m.p. 138° C, from 15.7 g (0.1 mole) of MHNI and 17.6 g (0.1 mole) of 2-chloro-4-nitrofluorobenzene.

EXAMPLE 105

1-Methyl-2(4-trifluoromethylphenoxymethyl)-5-nitro-imidazole, m.p. 95° C, from 15.7 g (0.1 mole) of MHNI and 16.4 g (0.1 mole) of 4-trifluoromethyl-fluorobenzene.

EXAMPLE 106

1-Methyl-2-(4-methylsulfonylphenoxymethyl)-5-nitro-imidazole, m.p. 157° C, from 15.7 g (0.1 mole) of MHNI and 17.4 g (0.1 mole) of 4-methylsulfonyl-fluorobenzene.

Process B

EXAMPLE 107

1-Methyl-2-(4-methylsulfonyl-phenoxymethyl)-5-nitro-imidazole 4-Methylthio-phenoxyacetaldehyde-diethylacetal (Formula VIII, $R^2$ = hydrogen, $R^3$ = 4-methylthio group, $R^4$ = ethyl)

152.5 Grams (1 mole) of chloroacetaldehyde-diethylacetal were heated at 100° C for 6 hours on the steam bath, together with 162 g (1 mole) of 4-methyl-thiophenol-sodium salt in 200 ml of dimethylacetamide (in a manner analogous to Comptes Rendus 194, 617 (1932)). After the precipitated sodium chloride had been suction-filtered, the solvent was removed by distillation under reduced pressure. 4-Methylthio-phenoxyacetaldehyde-diethylacetal was obtained as an oily residue which was directly further reacted.

4-Methylthio-phenoxyacetaldehyde (Formula IX, $R^2$, $R^3$ as specified above)

The above-mentioned compound was heated at 100° C for 1.5 hours, together with an excess of 70% formic acid. After the formic acid had been eliminated by distillation under reduced pressure, the raw aldehyde was obtained as an oil and was further utilized.

2-(4-Methylthio-phenoxymethyl)-imidazole (Formula X, $R^2$, $R^3$ as specified above)

182 Grams (1 mole) of 4-methylthio-phenoxyacetaldehyde (raw product) were dissolved in 600 ml of ethanol, 184 g of an aqueous glyoxal solution of 39% strength were added, were mixed with 284 ml of aqueous ammonia of 25% strength, and the reaction mixture was allowed to stand for 18 hours at room temperature. After evaporation under reduced pressure at 70° C, the residue was diluted with 400 ml of water and the pH value was adjusted to 1, while cooling with aqueous hydrochloric acid of 36% strength. The solution was shaken with chloroform, the acid phase was separated, was mixed with active charcoal, was filtered, was alkalized by means of aqueous ammonia of 25% strength, was then shaken three times with chloroform, the combined chloroform extracts were washed with water, dried over sodium sulfate and evaporated. The oily residue became solid in a crystalline form.

2-(4-Methylsulfonyl-phenoxymethyl)-imidazole (Formula X, R² = hydrogen, R³ = methylsulfonyl group)

115 Grams (1 mole) of 35% hydrogen superoxide were added dropwise, while stirring, to 110 g (0.5 mole) of 2-(4-methyl-thio-phenoxymethyl)-imidazole dissolved in 1000 ml of glacial acetic acid. By way of controlling the dropping rate, the exothermic reaction was maintained at a temperature of from 35° to 40° C. When the total amount had been added dropwise, the reaction mixture was allowed to stand for 15 hours at room temperature. Subsequently the glacial acetic acid was removed by distillation under reduced pressure, and the residue was recrystallized from isopropanol, while adding charcoal.

2-(4-Methylsulfonyl-phenoxymethyl)-4(5)-nitro-imidazole (Formula XI, R² = hydrogen, R³ = 4-methylsulfonyl group)

At a temperature not exceeding 15° C, 25.2 g (0.1 mole) of 2-(4-methylsulfonyl-phenoxymethyl)-imidazole were introduced, while stirring, into a mixture prepared at a temperature of from 0° to 5° C and consisting of 93 ml of acetic acid anhydride and 16.7 ml of 95% sulfuric acid. Into this reaction solution, 9.3 ml of 100% nitric acid were introduced dropwise, while stirring and cooling with ice and sodium chloride, at a temperature of from −5° to −8° C. Subsequently the mixture was stirred for 15 minutes at −5° C, and the reaction solution was then poured onto 300 g of ice. After the solution had been allowed to stand for 1 hour, the precipitate was suction-filtered, was dissolved in chloroform, and chromatographed over silica gel. The eluate was evaporated and the residue was recrystallized from ethanol, while adding charcoal.

1-Methyl-2-(4-methylsulfonyl-phenoxymethyl)-5-nitro-imidazole (Final product according to formula I, R¹ = methyl, R² = hydrogen, R³ = 4-methylsulfonyl group)

29.7 Grams (0.1 mole) of 2-(4-methylsulfonyl-phenoxymethyl)-4(5)-nitro-imidazole were heated at 90° C for 15 minutes, together with 29.2 g (0.23 mole) of dimethylsulfate. After the reaction mixture had been cooled, it was diluted with 200 ml of water, 20 g (0.23 mole) of sodium-hydrogen-carbonate were added portionwise, the precipitate formed was suction-filtered, was washed with water and was recrystallized from isopropanol, while adding charcoal. 1-Methyl-2-(4-methylsulfonyl-phenoxymethyl)-5-nitro-imidazole was obtained, which had a melting point of 155° C.

EXAMPLE 108

1-Methyl-2-(4-nitrophenoxymethyl)-5-nitro-imidazole

4-Nitrophenoxyacetaldehyde-diethylacetal from chloroacetaldehyde-diethylacetal and 4-nitrophenol-sodium salt.

4-Nitrophenoxyacetaldehyde from the above-specified compound by reaction with excess formic acid.

2-(4-Nitrophenoxymethyl)-imidazole from the above-specified compound by reaction with glyoxal and ammonia.

2-(4-Nitrophenoxymethyl)-4(5)-nitro-imidazole from the above-specified compound by nitration with concentrated nitric acid in concentrated sulfuric acid and acetanhydride and by subsequent chromatographic purification.

1-Methyl-2-(4-nitrophenoxymethyl)-5-nitro-imidazole from the above-specified compound by methylation with dimethylsulfate.

EXAMPLE 109

1-Methyl-2-(4-cyanophenoxymethyl)-5-nitro-imidazole

4-Cyanophenoxyacetaldehyde-diethylacetal from chloroacetaldehyde-diethylacetal and 4-cyanophenol-sodium salt.

4-Cyanophenoxyacetaldehyde from the above-specified compound by reaction with excess formic acid.

2-(4-Cyanophenoxymethyl)-imidazole from the above-specified compound by reaction with glyoxal and ammonia.

2-(4-Cyanophenoxymethyl)-4(5)-nitro-imidazole from the above-specified compound by nitration with concentrated nitric acid in concentrated sulfuric acid and acetic anhydride and by subsequent chromatographic purification.

EXAMPLE 110

1-Methyl-2-(4-trifluoromethyl-phenoxymethyl)-5-nitro-imidazole

4-Trifluoromethyl-phenoxyacetaldehyde-diethylacetal from chloroacetaldehyde-diethylacetal and 4-trifluoromethylphenol-sodium salt.

4-Trifluoromethylacetaldehyde from the above-specified compound by reaction with excess formic acid.

2-(4-Trifluoromethyl-phenoxymethyl)-imidazole from the above-specified compound by reaction with glyoxal and ammonia.

2-(4-Trifluoromethyl-phenoxymethyl)-4(5)-nitro-imidazole from the above-specified compound by nitration with concentrated nitric acid in concentrated sulfuric acid and acetic anhydride and by subsequent chromatographic purification.

1-Methyl-2-(4-trifluoromethyl-phenoxymethyl)-5-nitro-imidazole from the above-specified compound by methylation with dimethyl-sulfate.

We claim:

1. A 1-alkyl-2-(phenoxymethyl)-5-nitro-imidazole of the formula

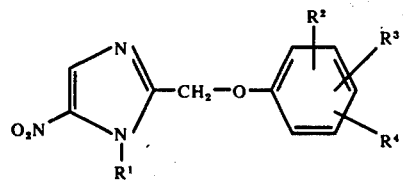

wherein R¹ is methyl or ethyl, R² is trifluoromethyl, trichloromethyl, nitro, cyano, methylsulfonyl, or ethylsulfonyl, R³ is hydrogen, fluorine, chlorine, bromine, iodine, trifluoromethyl, trichloromethyl, cyano or nitro, and R⁴ is hydrogen or methyl.

2. A compound as claimed in claim 1, which is 1-methyl-2-(4-nitrophenoxymethyl)-5-nitro-imidazole.

3. A compound as claimed in claim 1, which is 1-methyl-2-(4-cyano-phenoxymethyl)-5-nitro-imidazole.

4. A compound as claimed in claim 1, which is 1-methyl-2-(2-chloro-4-nitrophenoxymethyl)-5-nitro-imidazole.

5. A compound as claimed in claim 1, which is 1-methyl-2-(4-trifluoromethylphenoxymethyl)-5-nitro-imidazole.

6. A compound as claimed in claim 1, which is 1-methyl-2-(4-methylsulfonylphenoxymethyl)-5-nitro-imidazole.

7. A compound as claimed in claim 1, which is 1-methyl-2-(4-ethylsulfonylphenoxymethyl)-5-nitro-imidazole.

8. A compound as claimed in claim 1, which is 1-methyl-2-(2-trifluoromethyl-4-nitrophenoxymethyl)-5-nitro-imidazole.

9. A compound as claimed in claim 1, which is 1-methyl-2-(4-trifluoromethyl-2-nitrophenoxymethyl)-5-nitro-imidazole.

10. A compound as claimed in claim 1, which is 1-ethyl-2-(4-cyanophenoxymethyl)-5-nitro-imidazole.

11. A pharmaceutical preparation for the treatment of protozoal diseases, which preparation comprises an effective amount of a compound as claimed in claim 1 in combination with a pharmaceutically suitable carrier.

12. A method for treating protozoal diseases which comprises administering an effective amount of a compound as claimed in claim 1.

* * * * *